United States Patent [19]

Thunberg et al.

[11] Patent Number: 4,701,420

[45] Date of Patent: Oct. 20, 1987

[54] ANALYTICAL COMPOSITIONS, ELEMENTS AND METHODS UTILIZING REDUCTION OF FERRIC ION CHELATES TO FORM DETECTABLE DYES

[75] Inventors: Allen L. Thunberg, Pittsford; James A. Reczek, Rochester, both of N.Y.

[73] Assignee: Eastman Kodak Company, Rochester, N.Y.

[21] Appl. No.: 718,301

[22] Filed: Apr. 1, 1985

[51] Int. Cl.$^4$ ............................................. C12Q 1/32
[52] U.S. Cl. ..................................... 436/94; 422/56; 422/57; 422/60; 422/68; 435/26; 435/805; 436/904
[58] Field of Search ................ 436/94, 904, 169, 170; 422/56, 57, 60, 68; 435/26, 805

[56] References Cited

U.S. PATENT DOCUMENTS

| Re. 29,498 | 12/1977 | Meiattini | 195/103.5 |
|---|---|---|---|
| 3,095,382 | 6/1963 | Hach | 252/408 |
| 3,331,752 | 7/1967 | Struck et al. | 195/103.5 |
| 3,711,252 | 1/1973 | Roy | 422/56 |
| 3,887,332 | 6/1975 | Takase et al. | 23/230 |
| 3,954,412 | 5/1976 | Ogawa et al. | 23/253 |
| 4,101,381 | 7/1978 | Klose et al. | 195/99 |
| 4,116,774 | 9/1978 | Minato et al. | 195/99 |
| 4,224,034 | 9/1980 | Denney et al. | 23/230 |
| 4,245,041 | 1/1981 | Denney | 435/15 |
| 4,303,409 | 12/1981 | Ogawa et al. | 422/56 |
| 4,351,899 | 9/1982 | Owen | 435/26 |

FOREIGN PATENT DOCUMENTS 54-132527 10/1979 Japan .
58-052564 3/1983 Japan .
58-056698 4/1983 Japan .

OTHER PUBLICATIONS

*Research Disclosure*, publication 20149, vol. 201, Jan. 1981.

Smith, *Analytical Chemistry*, 26 (10), pp. 1534–1538 (1954).

*Primary Examiner*—Sidney Marantz
*Assistant Examiner*—David A. Saunders
*Attorney, Agent, or Firm*—J. Lanny Tucker

[57] ABSTRACT

Ferric ion chelates are useful in analytical compositions, elements and methods for the determination of reductants, or other analytes which can produce a reductant. The ferric ion chelate is reduced to ferrous ion, which coordinates with a suitable ferrous ion coordinating ligand to form a colored complex. In particular, these compositions and elments are useful for detecting nicotinamide adenine dinucleotide, reduced form (NADH) or nicotinamide adenine dinucleotide phosphate, reduced form (NADPH), or an analyte (e.g. an enzyme) which produces NADH or NADPH in biological fluids.

9 Claims, 3 Drawing Figures

ANALYTICAL COMPOSITIONS, ELEMENTS AND METHODS UTILIZING REDUCTION OF FERRIC ION CHELATES TO FORM DETECTABLE DYES

FIELD OF THE INVENTION

This invention relates to a novel composition, element and method for the analysis of liquids. In particular, reducible ferric ion chelates and ferrous ion coordinating ligands are used to produce a colored complex in response to a reductant. This invention is particularly useful in clinical chemistry to assay human biological fluids.

BACKGROUND OF THE INVENTION

A large number of clinically and biologically significant substances (e.g. enzymes) can be quantifiably determined using a reaction or sequence of reactions that generate a detectable reductant such as nicotinamide adenine dinucleotide, reduced form (hereinafter NADH) or nicotinamide adenine dinucleotide phosphate, reduced form (hereinafter NADPH). Most conventional assay methods which monitor either NADH or NADPH do so by directly measuring either the change in absorbance due to nicotinamide adenine dinucleotide (hereinafter, NAD) or nicotinamide adenine dinucleotide phosphate (hereinafter, NADP) when they are reduced, or by measuring the fluorescence change which occurs with that reduction.

These conventional procedures, however, present a number of problems. They are generally highly pH-sensitive and subject to considerable error if strict pH control is not maintained. Further, NADH and NADPH are relatively unstable compounds. Also, the sensitivity of such methods is relatively low due to the low extinction of NADH. These methods require the use of complicated optical equipment capable of operating in the ultraviolet region of the electromagnetic spectrum and are subject to interferences which arise in that region.

To improve the sensitivity of such assays and to avoid the problems with UV measurements, NAD or NADP reduction has been used with tetrazolium salts to yield formazan dyes. However, formazan dyes also have generally low extinction coefficients and the tetrazolium structures cannot be readily modified to increase the extinction.

U.S. Pat. No. 3,331,752 (issued July 18, 1967 to Struck, Jr. et al) describes a solution assay for enzymes which can be reacted to produce NADH. This assay uses a ferric ion chelate which is reduced by the NADH to form the corresponding ferrous ion chelate which has different absorption characteristics than its ferric ion counterpart. The ligand is the same material for both the ferric and ferrous chelates. This assay has a serious drawback, however. It is laborious and time-consuming since it requires a number of steps for successful completion. For example, enzyme reaction and NADH formation is carried out in solution at a suitable pH. After a desired time (5-20 minutes), the pH is changed by adding an acid or base to stop the enzyme reaction and resulting NADH formation. Simultaneously or subsequently to this, the ferric ion chelate is added to the mixture, and after another lengthy period of time, the resulting change in color of the ferrous ion chelate is measured. This laborious procedure is susceptible to inaccurate results and is not suitable for highly automated clinical procedures.

A triglycerides assay is described in U.S. Pat. No. 4,245,041 (issued Jan. 13, 1981 to Denney). In this assay, free ferric ions, an electron transfer agent, suitable triglyceride reagents and a ferrous ion chelating agent are mixed in a solution with the liquid sample. In the presence of triglycerides, the reaction sequence produces NADH which then reduces the ferric ions to ferrous ions which coordinate with the chelating agent. The resulting ferrous ion chelate is a colored dye which is easily detected. However, this assay presents a problem because uncomplexed ferric ions remaining in the composition are gradually reduced by undetermined reductants in the assay environment. Hence, the amount of ferrous ion chelate dye formed increases with time, causing inaccurate determinations. Further, if reagent blanks are used in calibrating the spectrophotometer used to measure the dye, the blanks can change with time and the instrument will have to be calibrated frequently. Clearly these disadvantages make this assay undesirable in view of the need for rapid, inexpensive and reliable assays in clinical laboratories today.

The problem of ferric ion instability in the triglycerides assay of Denney was noted in Japanese Patent Publication 56-153961 (published Apr. 4, 1983). This reference teaches the addition of a ferric ion masking agent (i.e. chelating agent) to the assay solution to complex with excess ferric ions and to allegedly arrest undesirable ferric ion reduction. This addition occurs after the assay for the analyte has been completed. Use of such a masking agent, however, requires that the assay conditions be carefully tailored so that the masking agent will chelate with the ferric ions. For example, the chelation is highly pH-dependent. So, the assay pH and the chelating agent pH must correspond in order for successful masking to occur, or the pH has to be changed when the masking agent is added. This procedure requires an additional step of adding the masking agent after dye formation, thereby complicating the assay and making it less desirable for highly automated analytical procedures.

In general, the ferric ion chelates described in the art are formed from weak chelating agents. Therefore, the ferrous ion chelating agents readily complex also with ferric ions, thereby making the ferric ions more easily reducible by reductants that may be present as interferents.

In view of the problems noted above with known assays, it would be desirable to have a simple, rapid and reliable assay for determining NADH, NADPH or similar reductants in highly automated analytical procedures.

SUMMARY OF THE INVENTION

The assay of the present invention solves the problems noted above using ferric ion chelates which can be reduced to produce ferrous ions which preferentially complex with a coordinating ligand to form a colored complex. Advantageously, the assay of this invention is simple to use (both in solution or dry analytical methods), rapid and highly reliable. In particular, it avoids the need to add masking agents after dye formation to stop undesired ferric ion reduction because unused ferric ions remain coordinated with the ferric ion chelate that is used in the assay. Further, the ferric ion chelates are formed from strong chelating agents. Thus, they are not readily reduced by mild reductants that may be present as interferents in the assay. The present invention provides an assay which can be reliably used in highly automated clinical analysis procedures.

Therefore, in accordance with this invention, a composition for the determination of a reductant in a liquid comprises:

(a) a chelate of ferric ions and a ferric ion coordinating ligand ($LIG_1$) which produces ferrous ions when reduced, and (b) a ferrous ion coordinating ligand ($LIG_2$) which preferentially coordinates ferrous ions to form a colored complex.

Another feature of this invention is a dry analytical element for the determination of a reductant (e.g. NADH or NADPH), or of an analyte which can react to produce such reductant, in a liquid. Such an element comprises an absorbent carrier material having therein the components (a) and (b) of the composition described in the preceding paragraph. The element can be designed to determine an analyte by including an interactive composition for such analyte therein.

Still another feature of this invention is a method for the determination of a reductant in a liquid. This method comprises the steps of:

A. physically contacting a sample of the liquid with (a) a chelate of ferric ions and a ferric ion coordinating ligand ($LIG_1$) which produces ferrous ions when reduced, (b) a ferrous ion coordinating ligand ($LIG_2$) which preferentially coordinates ferrous ions to form a colored complex, and B. detecting the colored complex.

DETAILED DESCRIPTION OF THE INVENTION

Figure 1:
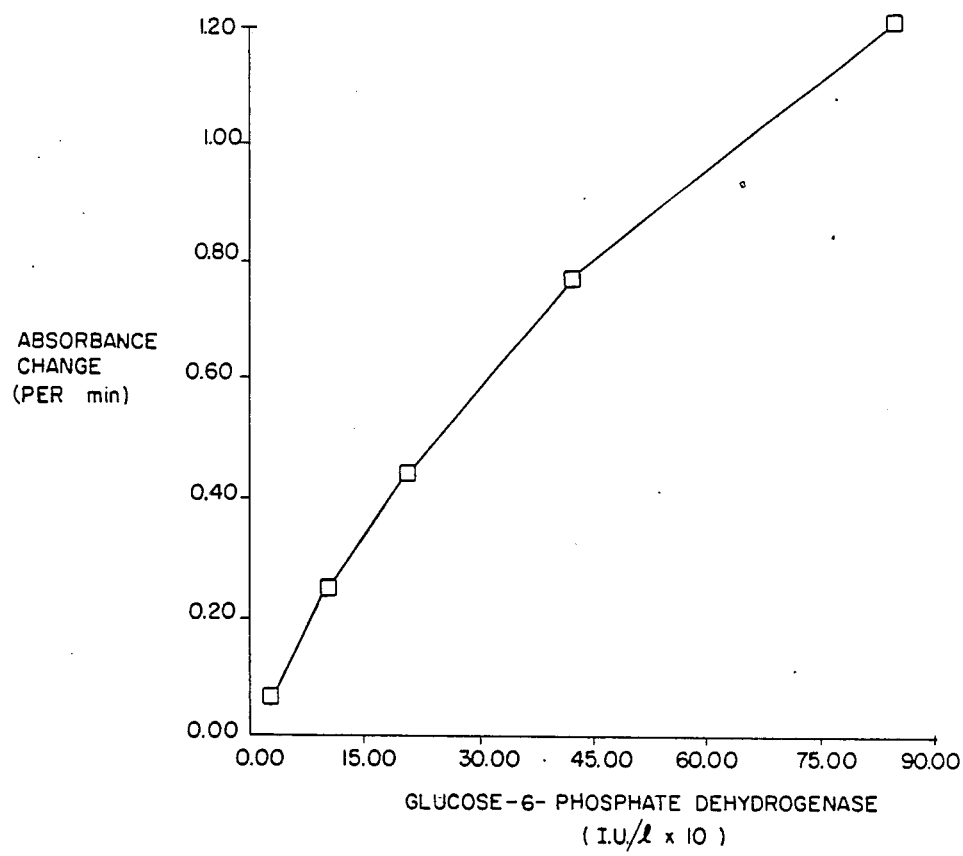
FIG. 1 is a graphical plot of the activity of glucose-6-phosphate dehydrogenase (I.U./1×10) vs. the reaction rate for that enzyme as expressed in change in absorbance (per minute) measured at 560 nm. This figure is discussed in Example 3 below.

This invention is useful for the determination of any reductant that can reduce Fe(III) to Fe(II). It is particularly useful for the determination of NADH or NADPH, or of analytes that generate NADH or NADPH by one or more enzymatic reactions. Such analytes include living cells (e.g. bacteria, yeast or fungi) and enzymes such as creatine kinase or dehydrogenases (e.g. glucose-6-phosphate dehydrogenase, lactate dehydrogenase and sorbitol dehydrogenase). Other analytes that can be detected with this invention are triglycerides, drugs (e.g. theophylline, phenobarbital, diphenylhydantoin and digoxin), antigens, antibodies or other immunologically reactive substances, enzyme substrates, and others known to one skilled in clinical chemistry. The invention can also be used to detect Fe(II) produced or left as residue in chemical or biochemical reactions, or occurring in aqueous liquids such as wastewater, ground water or cooling water.

The analytical compositions and elements of this invention contain a chelate of ferric ions and a ferric ion coordinating ligand ($LIG_1$), i.e. Fe(III)-$LIG_1$, which when reduced by a reductant, generates ferrous ions that preferentially coordinate with a ferrous ion coordinating ligand (described below) to provide a colored complex. $LIG_1$ is a compound containing one or more ferric ion coordinating ligand sites which complex with the ferric ions. The $LIG_1$ compounds do not preferentially complex with ferrous ions as compared to ferric ion. Examples of useful ferric ion coordinating ligands include iminodiacetic acid derivatives, o-hydroxybenzaldehyde, o-hydroxybenzoic acid derivatives, $\beta$-diketones, $\beta$-ketoesters, bipyridyl compounds, amines (primary, secondary, tertiary and cyclic), tertiary phosphines, mercaptans, thiourea derivatives, and the like.

$LIG_1$ can be a polymeric or nonpolymeric compound. Particularly useful nonpolymeric $LIG_1$ compounds are those having an iminodiacetic acid moiety (identified herein as iminodiacetic acid derivatives), such as iminodiacetic acid, ethylenediaminetetraacetic acid, N-(3-hydroxy-2-pyridylmethyl)iminodiacetic acid, diethylenetriaminepentaacetic acid, N-benzyliminodiacetic acid, trans-1,2-diaminocyclohexane-N,N,N',N'-tetraacetic acid, diethylenetriaminetetraacetic acid, 1,3-propylenediaminetetraacetic acid, nitrilotriacetic acid, cyclohexyldiaminetetraacetic acid, methyliminodiacetic acid, and the like.

Preferably, $LIG_1$ is a polymer containing one or more of the ferric ion coordinating moieties described above. Examples of such polymers are those containing the repeating units

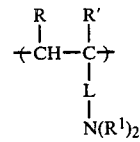

wherein R and R' are indepentently hydrogen, halo (fluoro, chloro, bromo or iodo) or substituted or unsubstituted alkyl, preferably of 1 to 6 carbon atoms (e.g. methyl, ethyl, isopropyl, chloromethyl, hydroxymethyl, hexyl, etc.). R is preferably hydrogen, and R' is preferably hydrogen or alkyl of 1 to 3 carbon atoms.

L is a bivalent linking group such as, but not limited to: substituted or unsubstituted alkylene, preferably of 1 to 6 carbon atoms (e.g. methylene, ethylene, propylene, tetramethylene, etc.), substituted or unsubstituted cycloalkylene, preferably of 5 to 10 carbon atoms in the ring nucleus (e.g. cyclopentylene, 1,4-cyclohexylene, 2-chloro-1,4-cyclohexylene, etc.), substituted or unsubstituted arylene, preferably of 6 to 10 carbon atoms in the nucleus (e.g. o-, m- or p-phenylene, 1,4-naphthylene, 2-chloro-p-phenylene, etc.), substituted or unsubstituted arylenealkylene, preferably of 7 to 12 carbon atoms in the backbone (e.g. phenylenemethylene, methylenephenylene, etc.),

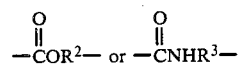

wherein $R^2$ and $R^3$ are independently alkylene, arylene or arylenealkylene as defined above. Preferably, L is arylenealkylene, and more preferably phenylenemethylene.

In the above polymeric structure, $R^1$ is a ferric ion coordinating moiety such as $-CHR^4COOM_1$, or $-CHR^4PO_3M_1M_2$ wherein $R^4$ is hydrogen or substituted or unsubstituted alkyl, preferably of 1 to 6 carbon atoms (e.g. methyl, hydroxymethyl, ethyl, hexyl, etc.), and $M_1$ and $M_2$ are independently suitable monovalent cations, such as hydrogen, an alkali metal or ammonium. More preferably, $R^1$ is $-CHR^4COOM_1$ and $R^4$ is hydrogen.

Other useful polymeric $LIG_1$ compounds include o-hydroxyaldehyde polymers such as poly[N-vinylbenzyl-N,N-dimethyl-N-(3-formyl-4-hydroxybenzyl)ammonium chloride] and the like, poly(vinylpyridines) such as poly(4-vinylpyridine), poly(2-vinylpyridine), poly(2-methyl-5-vinylpyridine) and the like, poly(vinylimidazoles) such as poly(N-vinylimidazole), poly(N-vinyl-2-methylimidazole), poly(N-vinyl-2-phenylimidazole) and the like, tertiary amine-containing polymers such as poly(N,N-dimethylaminoethyl methacrylate), poly(N-vinylbenzyl-N,N-dimethylamine) and the like, secondary amine-containing polymers such as poly(N-methyl-4-vinylaniline) and the like, primary amine-containing polymers such as poly(vinylaniline), poly(ethyleneimine), poly(2-aminoethyl methacrylate) and the like, and tertiary phosphine polymers such as poly(4-vinylphenyldiphenyl phosphine) and the like.

In addition, useful polymers include nitrogen-containing polymers quaternized with alkylating groups having appended ferric ion coordinating moieties, particularly polymers having recurring units of the structure

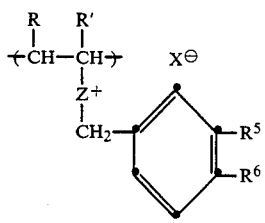

wherein R and R' are as defined above. $R^5$ and $R^6$ are independently ferric ion coordinating moieties such as $-OH$, $-COOH$, $-NHR^7$, $-NHCOR^8$, $-NHSO_2R^9$, $-SO_2NHR^7$ and the like wherein $R^8$ is substituted or unsubstituted alkyl preferably of 1 to 4 carbon atoms (methyl, hydroxymethyl, ethyl, etc.). $R^7$ is hydrogen or substituted or unsubstituted alkyl as defined for $R^8$. $R^9$ is substituted or unsubstituted alkyl as defined for $R^8$, or unsubstituted or substituted aryl preferably of 6 to 10 carbon atoms in the nucleus (e.g. phenyl, naphthyl, xylyl, etc.). Z represents the atoms necessary to complete a 5- to 13-membered, bivalent quaternary ammonium heterocyclic nucleus. X is a suitable anion such as chloride, bromide, iodide, methosulfate, p-toluenesulfonate, and the like.

Another class of polymers containing ferric ion coordinating moieties are active methylene group-containing polymers (i.e. polymers having pendant

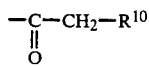

groups wherein $R^{10}$ is cyano or another electron-withdrawing substituent such as

wherein $R^{11}$ is substituted or unsubstituted alkyl, alkoxy, aryloxy, aryl or aralkyl all of which can be defined similarly to the groups defined above for L).

Particularly preferred polymers containing moieties which will coordinate with ferric ions are polymers comprising from about 5 to 100 weight percent of the recurring units having the structure

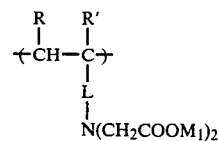

wherein R, R', L and $M_1$ are defined above. These polymers are also known as iminodiacetic acid derivatives. A useful polymeric iminodiacetic acid derivative is poly[N-(m and p-vinylbenzyl)iminodiacetic acid].

The $LIG_1$ compounds described above are either commercially available or prepared by one skilled in synthetic chemistry using known starting materials and procedures. For example, details of preparation of the described polymers are given in *Research Disclosure*, publication 18534, September, 1979, pp. 505–512 and the references cited therein. *Research Disclosure* is currently available from Kenneth Mason Publications, Ltd., The Old Harbourmaster's, 8 North Street, Emsworth, Hampshire P010 7DD England.

The polymers described above can also contain up to 95 weight percent, but preferably up to about 50 weight percent, of recurring units derived from one or more polymerizable ethylenically unsaturated monomers other than the monomers described above. Such monomers include, but are not limited to, styrene and related aromatic monomers, acrylic and methacrylic acids and esters, vinyl amides, sulfoalkyl acrylic esters or amides and others within the skill of a polymer chemist.

In the context of this application, the term "coordinate" refers to the sharing of electron pairs by the ferric or ferrous ions and the $LIG_1$ or $LIG_2$ compound, respectively. The stability constant for the respective chelates can be determined by conventional procedures noted in *Research Disclosure* publication 18534 noted above.

Ferric ions and $LIG_1$ form a suitable chelate when mixed in a suitable vessel. Chelation generally proceeds at ambient temperatures and without the aid of a catalyst.

The composition of this invention optionally, but preferably, includes an electron transfer agent (identified herein as ETA) which can transfer electrons from the reductant to the ferric ions of the ferric ion chelate. In general, the ETA has a reduction potential ($E_{\frac{1}{2}}$) which is more positive than the $E_{\frac{1}{2}}$ of the ferric ion chelate and is less positive than that of the reductant, as measured in water. $E_{\frac{1}{2}}$ measurements are made according to conventional electrochemical techniques using differential pulse polarography or cyclic voltametry (see, e.g. Sawyer and Roberts, Jr., *Experimental Electrochemistry for Chemists*, John Wiley & Sons, New York, 1974).

ETA compounds useful in the practice of this invention include phenazine methosulfate, phenazine ethosulfate, and similar compounds, and substituted ethosulfate, and similar compounds, and substituted benzoquinones and naphthoquinones such as those described in copending and commonly assigned U.S. Ser. No. 699,374, filed Feb. 7, 1985 by A. J. Mura et al and entitled USE OF SUBSTITUTED QUINONE ELECTRON TRANSFER AGENTS IN ANALYTICAL DETERMINATIONS. Combinations of different ETA compounds can be used if desired. Phenazine methosulfate is a preferred ETA.

The composition of this invention further comprises a ferrous ion coordinating ligand ($LIG_2$) which is a compound which preferentially complexes with ferrous ions to form a colored complex. Generally, the colored complexes so formed absorb electromagnetic radiation in the visible portion of the electromagnetic spectrum, i.e. between about 400 and about 700 nm. More than one molecule of $LIG_2$ can complex with a single ferrous ion. These $LIG_2$ compounds do not form chelates with ferric ions to any appreciable extent.

Useful nonpolymeric $LIG_2$ compounds are ferroine, cuproine and terroine type compounds such as those described by Smith in *Analyt. Chem.*, 26, pp. 1534–1538, 1954, hydrazones, tetrazolylpyridines, pyridylquinazolines, bis-isoquinolines, imines, phenanthrolines, bipyridines, terpyridines, bidiazines, pyridyldiazines, pyridylbenzimidazoles, diazyltriazines, o-nitrosoanilines, phenols, tetrazines, triazines described by Schilt et al in the journal *Talanta*, 15, pp. 475–478 (1968), pyridine derivatives of phenazine and quinoxaline described by Schilt et al in *Talanta*, 15, pp. 852–855 (1968), substituted benzimidazole derivatives as described by Schilt et al, *Talanta*, 15, pp. 1055–1058 (1968), oximes of substituted methyl and phenyl 2-pyridyl ketones as described by Schilt et al, *Talanta*, 16, pp. 448–452 (1969), and the like. Other $LIG_2$ compounds are described in the following *Talanta* literature articles: 16, pp. 519–522 (1969), 13, pp. 895–902 (1966), 17, pp. 649–653 (1970), 19, pp. 1025–1031 (1972), 21, pp. 831–836 (1974), 22, pp. 915–917 (1975), 23, pp. 543–545 (1976), 24, pp. 685–687 (1977), 26, pp. 85–89 (1979), pp. 863–865 (1981), 36, pp. 373–376 (1979), 55, pp. 55–58 (1980), 29, pp. 129–132 (1982), and in Blandamer et al, *J. Chem. Soc. Dalton*, pp. 1001–1008 (1978), Case, *J. Org. Chem.*, 31, pp. 2398–2400 (1966) and U.K. Pat. No. 701,843 (published Jan. 6, 1954).

The nonpolymeric $LIG_2$ compounds can have a ballast group which renders it nondiffusible in an analytical element during the assay. Useful ballast groups are generally organic groups of such molecular size and configuration as to render the compound nondiffusable in an element. Particularly useful groups include long chain alkyl groups (e.g. 6 to 30 carbon atoms), as well as aromatic groups (phenyl, naphthyl) along with alkyl groups. Representative ballast groups include $-CO-C_{11}H_{23}$, $-CO-C_6H_4(t-C_{12}H_{25})$, $-CON(C_{12}H_{25})_2$,

$-SO_2C_{16}H_{33}$, $-C_7H_{15}$, and $-\langle\rangle-NHSO_2C_{16}H_{33}$.

Other groups also contain solubilizing groups, e.g.

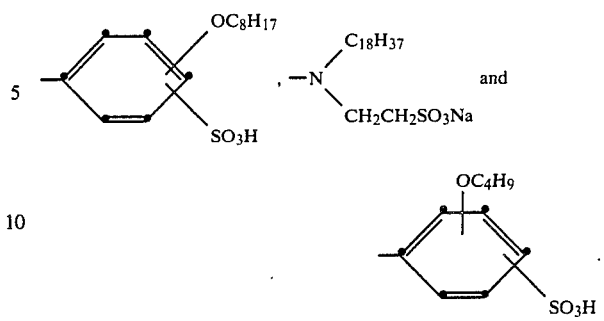

Alternatively, the $LIG_2$ compound can be a polymer chain which has one or more ferrous ion coordinating moieties attached to the polymer backbone in a suitable manner. These polymers are generally bulky enough to be immobile in a coated layer, i.e. they are self-ballasting.

Polymers to which ferrous ion coordinating moieties can be attached are those having reactive groups that readily react with complementary reactive groups on a nonpolymeric $LIG_2$ compound or are polymerized from monomers containing such moieties. For example, groups which easily undergo condensation reactions are quite useful. Acid derivatives including free carboxylic acids, acid chlorides and anhydrides readily condense with hydroxy, amine, and mercapto groups to split out small molecules and form the desired monomer or polymer condensation product. The same can be accomplished with addition reactions, e.g. a hydroxy or amine group adds readily to an isocyanate group to form urethane or urylene linkages, or an activated unsaturated group (acryloyl) adds readily to an amine group, or by any other reactions known in the art. The monomers can then be polymerized to form the polymers using conventional polymerization techniques. Thus, any polymers or monomers, preferably vinyl polymers or monomers, containing requisite reactive groups complementary to reaction groups on the nonpolymeric $LIG_2$ compound to be attached to the polymer are useful in forming polymeric $LIG_2$ compounds or monomers useful in making same. Polymers and monomers containing carboxylic acid, carboxylic acid halides, carboxylic acid anhydride, sulfonic acid, hydroxy, epoxy, amino, isocyanate, etc. groups are especially useful. More specifically, copolymers of acrylic acid, methacrylic acid, maleic anhydride, 2-hydroxyethyl acrylate, glycidyl methacrylate, and the like, have useful reactive groups. The preparation and properties of such polymers are given in various polymer textbooks such as M. P. Stevens *Polymer Chemistry An Introduction*, Addison-Wesley Publishing Co., Inc., Reading, Mass. (1975) and W. A. Sorenson and T. W. Campbell, *Preparative Methods of Polymer Chemistry*, 2nd Ed., Wiley, New York, N.Y. (1968). Comonomers useful in preparing the polymeric $LIG_2$ compounds can be any that are compatible with the preparative reactions involved and whose substituents do not interfere with the analytical process. Acrylamide, acrylamide derivatives and other hydrophilic comonomers are particularly useful.

Particularly useful $LIG_2$ compounds (polymeric or nonpolymeric) have one or more coordinating moieties which are represented by the structure $$Z-\overset{R^{12}}{\underset{(H)_n}{C}}-(\overset{R^{15}}{C}=N-\overset{R^{16}}{\underset{(H)_p}{C}})_{\overline{m}}-\overset{R^{13}}{C}=N-R^{14}$$

In this structure, m is 0 or a positive integer of 1 to 3, n and p are independently 0 or 1, and $\doteq$ represents a single or double bond. Z is R''—N═, O═, S═, R''—P═, (R'')$_2$P— or (R'')$_3$P═, and when Z is (R'')$_2$P—, n is 1, otherwise n is 0. Preferably, m is 0 or 1 and Z is R''—N═.

R'', R$^{12}$, R$^{13}$, R$^{14}$, R$^{15}$ and R$^{16}$ are independently hydrogen, amino (primary, secondary or tertiary), hydroxy, mercapto, alkoxy (preferably of 1 to 20 carbon atoms, e.g. methoxy, chloromethoxy, ethoxy, octyloxy, alkoxy substituted with imino, etc.), alkyl (preferably of 1 to 20 carbon atoms in the nucleus, e.g. methyl, ethyl, chloromethyl, isopropyl, t-butyl, heptyl, alkyl substituted with imino, etc.), aryl (preferably of 6 to 14 carbon atoms, e.g. phenyl, naphthyl, xylyl, p-methoxyphenyl, aryl substituted with imino, etc.), or a heterocyclic moiety (preferably having 5 to 20 carbon, nitrogen, sulfur or oxygen atoms in the nucleus, e.g. pyridyl, quinolyl, a heterocycle substituted with imino, etc.).

When R$^{16}$ is a group defined above, p is 1 and $\doteq$ is a single bond.

Alternatively, if m is 0, R'' and R$^{12}$, R$^{12}$ and R$^{13}$, and R$^{13}$ and R$^{14}$, taken together, can independently represent the carbon atoms and heteroatoms (e.g. nitrogen, oxygen, sulfur, selenium, etc.) necessary to complete a substituted or unsubstituted 5- to 20-membered mono- or polycyclic heterocyclic nucleus (e.g. pyridyl, quinolyl, triazinyl, phenanthrolinyl, pyrimidyl, etc.). R$^{12}$ and R$^{13}$, taken together, can also represent the carbon atoms necessary to complete a substituted or unsubstituted 5- to 20-membered mono- or polycyclic carbocyclic nucleus (e.g. phenyl, naphthyl, etc.). The nucleus so formed can be substituted with one or more oxo, alkyl, amino, imino, aryl, phosphino (e.g. diphenylphosphino), alkoxy, amide, sulfonamide, thio or sulfo groups as defined above or a heterocyclic group (e.g. pyridyl, pyrimidyl, thiazolyl, imidazolyl, thienyl, etc.).

If m is 1, 2 or 3, R'' and R$^{12}$, R$^{15}$ and R$^{16}$ and R$^{13}$ and R$^{14}$, taken together, can represent the carbon and heteroatoms (e.g. nitrogen, oxygen, sulfur, selenium, etc.) necessary to complete a substituted or unsubstituted 5 to 20 membered mono- or polycyclic heterocyclic nucleus as defined above where m is 0. When R$^{15}$ and R$^{16}$ are so defined, p is 0 when $\doteq$ is a double bond, and p is 1 when $\doteq$ is a single bond.

Examples of useful nonpolymeric LIG$_2$ compounds which form colored complexes with ferrous ions include the following (the $\lambda_{max}$ of each resulting colored complex is also noted):

magenta, $\lambda_{max}$ = 560 nm cyan, $\lambda_{max}$ = 650 nm $$H_2N-N=\overset{H_3C}{\underset{|}{C}}-\overset{CH_3}{\underset{|}{C}}=N-NH_2$$
yellow, $\lambda_{max}$ = 442 nm, $$H_2N-N=\overset{H_{15}C_7}{\underset{|}{C}}-\overset{C_7H_{15}}{\underset{|}{C}}=N-NH_2$$
yellow, $\lambda_{max}$ = 443 nm, yellow, $\lambda_{max}$ = 441 nm, $$H_3C-N=\overset{H_3C}{\underset{|}{C}}-\overset{CH_3}{\underset{|}{C}}=N-CH_3$$
magenta, $\lambda_{max}$ 564 nm, magenta, $\lambda_{max}$ = 522 nm, magenta, $\lambda_{max}$ = 552 nm, magenta, $\lambda_{max}$ = 557 nm, magenta, $\lambda_{max}$ = 571 nm, -continued

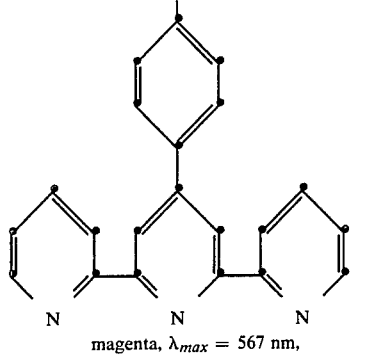

magenta, $\lambda_{max} = 567$ nm,

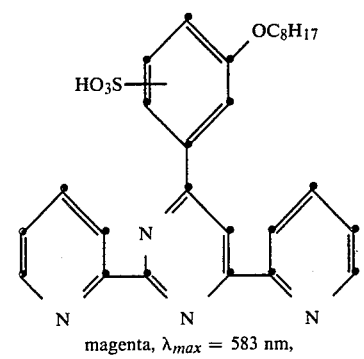

magenta, $\lambda_{max} = 583$ nm,

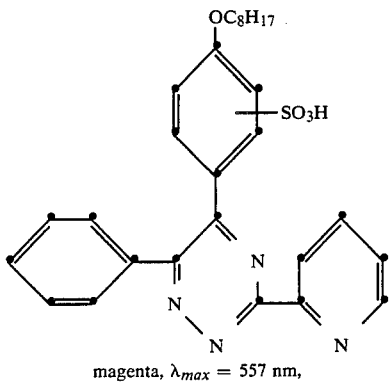

magenta, $\lambda_{max} = 557$ nm,

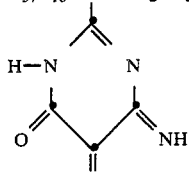

cyan, $\lambda_{max} = 644$ nm,

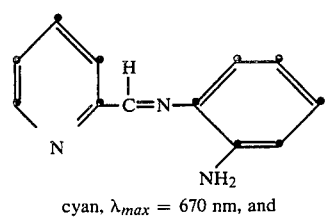

cyan, $\lambda_{max} = 670$ nm, and

-continued

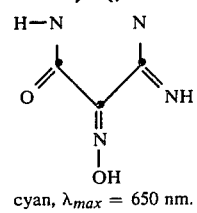

cyan, $\lambda_{max} = 650$ nm.

Polymers useful as LIG$_2$ compounds are represented by the following structure:

$$-(CH_2-CH)_x-(CH_2-CH)_y-(CH_2-C)_z-$$

with pendant groups CONH$_2$, CONHCH$_2$CH$_2$O-[pyridyl terpyridine], W, and CONH-(CH$_2$)$_3$NH$_2$·HCl wherein W is hydrogen or methyl, x is 0 to about 98 weight percent, y is from about 2 to about 60 weight percent, and z is 0 to about 40 weight percent, magenta, $\lambda_{max}=561$ nm wherein W is hydrogen, x is 65, y is 30 and z is 5.

The first LIG$_2$ compound illustrated above (ferrozine) is preferred in the practice of this invention.

The LIG$_2$ compounds useful in the practice of this invention can be either obtained commercially or prepared using starting materials and techniques known in the art. See, for example the Talanta references noted above as well as U.K. Pat. No. 701,843 relating to non-polymeric compounds. Polymeric compounds are easily prepared as described above using conventional synthetic methods.

The analytical composition of this invention can be used in both solution and dry element assays to detect or quantify an analyte (e.g. defined above). Reductants which can be determined with this invention include, but are not limited to, NADH, NADPH, flavin adenine dinucleotide (reduced form) (FADH), flavin mononucleotide (reduced form) (FMNH), thiols, such as dithiothreitol, dithioerythritol and 2-mercaptoethanol, and living cells, such as yeast and bacteria. The analytical composition can be prepared for use in a solution assay by mixing the Fe(III)-LIG$_1$ chelate, the LIG$_2$ compound, and optionally the ETA, in water. The details of preparing a representative analytical composition are given in Example 1 below. Other optional components can also be included in the compositions, including buffers, surfactants, interactive compositions (described below), etc.

When the compositions of this invention are used in solution assays, generally the Fe(III)-LIG$_1$ chelate is present in a concentration of up to about 10, and preferably from about 0.06 to about 1.2, mg/ml of solution. When used, the ETA is present in an amount up to 0.3, and preferably from about $5 \times 10^{-4}$ to about 0.01, mg/ml. The LIG$_2$ compound is generally present in an amount up to 20, and preferably from about 0.5 to about 5, mg/ml. When NADH or NADPH are determined in response to the presence of another analyte in the assayed sample, the corresponding oxidized form, NAD or NADP, is generally added to the solution in an amount to provide up to about 10, and preferably from about 0.2 to about 2.5, mg/ml. The amounts of the other optional composition components (e.g. buffer, surfactant, etc.) and of the interactive composition (described below) are readily determined by one skilled in the clinical chemistry art.

The compositions of this invention can be used to determine an analyte which is capable of producing NADH or NADPH by a reaction or series of reactions by including an interactive composition in such compositions which produces the reductant. Analytes which can be determined in this manner include, but are not limited to, triglycerides, dehydrogenases, creatine kinase, and others known to one skilled in the clinical chemistry art. The composition of this invention can also be used in competitive binding assays for determining immunologically reactive substances.

This invention is adaptable to both solution and dry element assays. In a solution assay, generally the Fe(III)-$LIG_1$ chelate, ETA (if used), $LIG_2$ compound and interactive composition (if included) are physically contacted and mixed with a liquid test sample in a suitable container (e.g. test tube, petrie dish, beaker, cuvette, etc.). The resulting solution can be incubated, if desired, for a suitable time at a suitable temperature. The sample is then evaluated by measuring the amount of colored complex produced upon coordination of $LIG_2$ and ferrous ions. The amount of colored complex detected can be correlated to the amount of reductant (e.g. NADH or NADPH) either initially present in the sample, or produced as a result of the presence of an analyte. Such an evaluation can be done visually or with suitable colorimetric detection equipment and procedures.

Alternatively, the composition and method of this invention can be utilized with a dry analytical element which comprises an absorbent carrier material (e.g. a thin sheet of a self-supporting absorbent or bibulous material, such as filter paper or paper test strips) and the components of the composition described above. Such elements can also contain an interactive composition for the analyte. These elements are known in the art as test strips, diagnostic elements, dip sticks, diagnostic agents and the like.

When employed in dry analytical elements, the composition components can be incorporated into the absorbent carrier material by imbibition, impregnation, coating or another suitable technique. Useful absorbent carrier materials are insoluble and maintain their structural integrity when exposed to water or physiological fluids such as urine or serum. Useful absorbent carrier materials can be prepared from paper, porous particulate structures, porous polymers, cellulose, wood, glass fiber, woven and nonwoven fabrics (synthetic and nonsynthetic) and the like. A useful dry analytical element is made by imbibing a solution of the composition into the material and drying. Details for making such elements are well known in the art, as exemplified in U.S. Pat. Nos. 3,092,465 (issued June 4, 1963 to Adams et al), 3,802,842 (issued Apr. 9, 1974 to Lange et al), 3,915,647 (issued Oct. 28, 1975 to Wright), 3,917,453 (issued Nov. 4, 1975 to Milligan et al), 3,936,357 (issued Feb. 3, 1976 to Milligan et al), 4,248,829 (issued Feb. 3, 1981 to Kitajima et al), 4,255,384 (issued Mar. 10, 1981 Kitajima et al), and 4,270,920 (issued June 2, 1981 to Kondo et al), and U.K. Pat. No. 2,052,057 (published Jan. 21, 1981).

Preferably, the dry analytical elements of this invention have at least one porous spreading zone as the carrier material. This zone, alone or with other zones, can be self-supporting (i.e. composed of a material rigid enough to maintain its integrity), but preferably it is carried on a separate supporting substrate (commonly called a support). Such a support can be any suitable dimensionally stable, and preferably, transparent (i.e. radiation transmissive) material which transmits electromagnetic radiation of a wavelength between about 200 and about 900 nm. A support of choice for a particular element should be compatible with the intended mode of detection (reflection or transmission spectroscopy). Useful support materials include paper, metal foils, polystyrene, polyesters [e.g. poly(ethylene terephthalate)], polycarbonates, cellulose esters (e.g. cellulose acetate), etc.

The porous spreading zone can be prepared from any suitable fibrous or non-fibrous material or mixtures of either or both. The void volume and average pore size of this zone can be varied depending upon the use intended. For example, if whole blood or other liquid samples containing high molecular weight materials are to be assayed, the void volume and average pore size are generally greater than if serum or urine is to be assayed.

Useful spreading zones can be prepared using fibrous materials, either mixed with a suitable binder material or woven into a fabric, as described in U.S. Pat. No. 4,292,272 (issued Sept. 29, 1981 to Kitajima et al). Alternatively, and preferably, the spreading zone is prepared from polymeric compositions (e.g. blush polymers) or particulate materials, with or without binding adhesives, as described in U.S. Pat. Nos. 3,992,158 (issued Nov. 16, 1976 to Przybylowicz et al) and 4,258,001 (issued Mar. 24, 1981 to Pierce et al). Other useful spreading zone materials are described in W. German OLS No. 3,150,102 (published July 29, 1982) and Japanese Patent Publication No. 57(1982)-101760 (published June 24, 1982), both assigned to Konishiroku Photo. It is desirable that the spreading zone be isotropically porous, meaning that the porosity is the same in each direction in the zone as created by interconnected spaces or pores between particles, fibers, polymeric strands, etc.

The elements can have more than one zone, e.g. one or more reagent zones, spreading zones, registration zone, mordant zone, radiation-blocking (or filter) zone, subbing zone, barrier zone, buffer zone, etc. The zones are generally in fluid contact with each other meaning that fluids, reagents and reaction products can pass between superposed regions of adjacent zones unless the zones are designed to inhibit the passing of certain materials. Preferably, the zones are separately coated layers, although two or more zones can be a single layer, or a zone can contain two or more separate layers. Besides the references noted above, suitable element formats and components are described, for example, in U.S. Pat. No. 4,042,335 (issued Aug. 16, 1977 to Clément), 4,132,528 (issued Jan. 2, 1979 to Eikenberry et al), and 4,144,306 (issued Mar. 13, 1979 to Figueras).

The components of the compositions of this invention, i.e. Fe(III)-$LIG_1$ chelate, ETA (if present), $LIG_2$ compound, interactive composition (if present), and other optional components can be incorporated in any of the zones of the elements that would be suitable for the particular analysis. For example, a mordant may be useful in the zone containing the resulting dye to reduce its tendency to wander. The location of individual components is within the skill of a worker in the clinical chemistry art.

In the elements of this invention, the amount of the $Fe(III)$-$LIG_1$ chelate can be varied widely, but it is generally present in a coverage of up to about 10, and preferably from about 0.2 to about 2 $g/m^2$. The ETA (if used) is present in a coverage of up to about 1, and preferably from about 0.01 to about 0.1 $g/m^2$. The $LIG_2$ compound is generally present in an amount of up to about 10, and preferably from about 0.2 to about 2, $g/m^2$. When NADH and NADPH are the reductants being determined in response to an analyte, the corresponding oxidized forms, NAD or NADP are generally present in the element in an amount of up to about 8, and preferably from about 0.3 to about 2.5, $g/m^2$. A variety of other desirable, but optional reagents and addenda can be present in the element in amounts known to one skilled in the art. Such materials include surfactants, buffers, binders, pigments, activators, mordants, subbing materials, reagents for the interactive compositions, etc.

One embodiment of this invention is a multilayer dry analytical element for determining an analyte. This element comprises a support having thereon, in order and in fluid contact, a registration layer containing a hydrophilic binder material (natural or synthetic), such as gelatin or polyacrylamide, and a porous spreading layer. The element also comprises: (1) an interactive composition which produces NADH or NADPH upon interaction with the analyte, (2) a $Fe(III)$-$LIG_1$ chelate as described above, (3) an ETA as described above, and (4) a $LIG_2$ compound as described above. This element can also include a mordant layer between the registration and spreading layers. This layer can contain one or more polymeric mordants, such as those described in U.S. Pat. No. 4,166,093 (issued Aug. 28, 1979 to Smith-Lewis et al).

A variety of different elements, depending on the method of assay, can be prepared in accordance with the present invention. Elements can be configured in a variety of forms, including elongated tapes of any desired width, sheets, slides or chips.

The assay of this invention can be manual or automated. In using the dry elements, the determination is made by taking the element from a supply roll, chip packet or other source and physically contacting it with a sample (e.g. 1–100 $\mu l$) of the aqueous liquid to be tested. Such contact can be accomplished in any suitable manner, e.g. dipping or immersing the element into the sample or, preferably, by spotting the element by hand or machine with a drop of the sample with a suitable dispensing means.

After sample application, the element is exposed to any conditioning, such as incubation, heating or the like, that may be desirable to quicken or otherwise facilitate obtaining any test result.

Determination of the reductant (e.g. NADH, NADPH) or an analyte is achieved when the $LIG_2$ compound coordinates with ferrous ions to provide a detectable colored complex. This complex can be detected visually or with suitable spectrophotometric means and procedures.

In the following examples, the materials used were obtained as follows: glucose-6-phosphate, NADH from Sigma Chemical Co. (St. Louis, Mo.), bovine serum albumin from Miles Laboratories, Inc. (Elkhart, Ind.), diethylenetriaminepentaacetic acid from Aldrich Chemical Co. (Milwaukee, Wis.), glucose-6-phosphate dehydrogenase from Genzyme (Norwalk, Conn.), theophylline antibodies from Kallested Laboratories (Chaska, Minn.), Estane TM polyurethane resin from B. F. Goodrich (Cleveland, Ohio), Triton TM X-100 surfactant from Rohm and Haas (Philadelphia, Pa.), and the remainder from Eastman Kodak Company (Rochester, N.Y.) or prepared using known starting materials and procedures.

The following Examples illustrate the practice of this invention.

EXAMPLE 1

Determination of NADH in Solution Assay Using Various $Fe(III)$-$LIG_1$ Compounds Several $Fe(III)$-$LIG_1$ chelates were used in solution assays to determine NADH in the following manner. A 2 millimolar stock solution of NADH was diluted to obtain samples of stock solutions having NADH concentrations ranging from 0.031 to 0.2 millimolar. Each of these solutions was then diluted 1:20 in 0.1 molar $KH_2PO_4$ buffer (pH 6.5) and the absorbance of NADH was determined using a conventional spectrophotometer at 340 nm.

Three sets of solutions were prepared as follows, each having a different $LIG_1$:

Solution 1

N-(3-hydroxy-2-pyridylmethyl)iminodiacetic acid ($LIG_1$), ferrozine ($LIG_2$) and $Fe(NO_3)_3.9H_2O$ were dissolved in distilled water to achieve solution having concentrations of 0.24 mg/ml (1 millimolar), 2.55 g/ml (5 millimolar) and 0.4 mg/ml (1 millimolar), respectively.

Solution 2

This solution was prepared the same as Solution 1, except that $LIG_1$ was diethylenetriaminepentaacetic acid. Gentle heating or sonication was used to improve dissolution of $LIG_1$.

Solution 3

Poly[N-(m and p-vinylbenzyl)iminodiacetic acid] (48 g) ($LIG_1$) was added to 10 ml of distilled water. To dissolve the polymer, the pH was adjusted to a value greater than 12 by the addition of about 5 ml of 1 normal NaOH. The pH was subsequently adjusted to 4 with 1 normal HCl and sufficient $Fe(NO_3)_3.9H_2O$ was added to give a final concentration of 0.001 molar ferric ion chelate. NaOH was again added to adjust the pH to about 10 and to clarify the solution (complete chelation). After adjusting the pH to about 7 with HCl, 0.005 molar ferrozine ($LIG_2$) was added, and the pH was neutralized to 7 with NaOH.

All of the above chelate solutions were diluted 1:5 with water. A 50 $\mu l$ sample of each NADH stock solution was diluted 1:20 with each diluted chelate solution to form an assay solution. Diluted chelate solutions without NADH were used as Controls. A 50 $\mu l$ sample of 0.2 millimolar phenazine methosulfate (ETA) was added to 950 $\mu l$ of each assay solution and the absorbances (A) of the resulting mixtures were measured at 560 nm with a conventional spectrophotometer. The absorbance of a control solution (no ferrozine) was subtracted from the absorbance of each assay solution. The data obtained is presented in Table I below. Much higher absorbances were obtained using ferrozine registration (at 560 nm) of NADH with various Fe(III)-LIG$_1$ compounds as compared to direct NADH detection at 340 nm. These results demonstrate the advantage of the present invention with several Fe(III)-LIG$_1$ compounds.

TABLE I

| Millimolar NADH | $A_{340\ nm}$ | $A_{560\ nm}$Fe(II)LIG$_2$ | | |
|---|---|---|---|---|
| | | Sol. 1 | Sol. 2 | Sol. 3 |
| 2.0 | 0.627 | 3.370 | 3.400 | 3.300 |
| 1.0 | 0.339 | 2.480 | 2.340 | 2.150 |
| 0.5 | 0.190 | 1.352 | 1.316 | 1.250 |
| 0.25 | 0.117 | 0.747 | 0.770 | 0.710 |
| 0.13 | 0.079 | 0.468 | 0.503 | 0.444 |
| 0.063 | 0.062 | 0.305 | 0.376 | 0.314 |
| 0.031 | 0.051 | 0.237 | 0.313 | 0.245 |
| H$_2$O Blank | — | 0.083 | 0.101 | 0.080 |

EXAMPLE 2

Determination of NADH in Solution Assay With Various Fe(II)-LIG$_2$ Complexes

This example demonstrates the use of several LIG$_2$ compounds to determine NADH:

Ferrozine A.

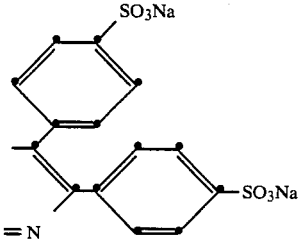

N-(6-amino-4-hydroxy-5-nitroso-2-pyrimidyl)-N—octadecyltaurine B.

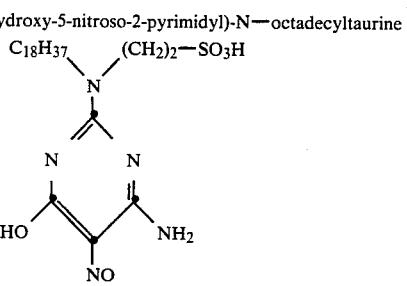

4-(3-sulfonyl-4-n-butoxy)phenyl-2,6-di(2-pyridyl)-pyridine C.

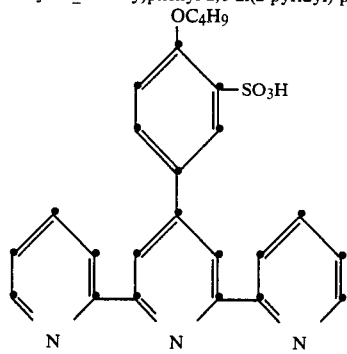

Biacetyldihydrazone D.

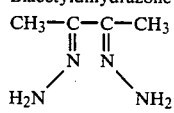

An aqueous ferric chelate solution containing 0.001 molar N-(3-hydroxy-2-pyridylmethyl)iminodiacetic acid (LIG$_1$) and 0.001 molar Fe(NO$_3$)$_3$.9H$_2$O was prepared. To separate 5 ml aliquots of this solution was added each of the LIG$_2$ ligands (A, B, C, and D identified above) to achieve an assay solution having a LIG$_2$ concentration of 0.005 molar. During LIG$_2$ addition, the pH of the solution was kept below 6.0. Compound C was first dissolved in 5 ml of 20% pyridine prior to the addition of 5 ml of the above chelate solution. All of the assay solutions were subsequently diluted to 25 ml with distilled water. Blank solutions without LIG$_2$ were also prepared for background measurements. To perform the assay, 50 µl of each NADH stock solution (2 millimolar to 0.003 millimolar) prepared as in Example 1 and 50 µl of 0.2 millimolar phenazine methosulfate (ETA) were added to 900 µl of each of the above solutions. Control solutions lacking NADH were also prepared. The absorbance of each assay solution was measured at the wavelengths indicated in Table II for each LIG$_2$ compound. The absorbances were corrected by subtracting the absorbance of a control solution without LIG$_2$.

The data of Table II indicate that all of the LIG$_2$ compounds were useful for NADH determination although maximum response was obtained with compounds A and C.

TABLE II

| Millimolar NADH | LIG$_2$ Absorbance | | | |
|---|---|---|---|---|
| | A 560 nm | B 650 nm | C 575 nm | D 450 nm |
| 2.0 | 3.250 | 2.353 | 3.280 | 0.349 |
| 1.0 | 2.110 | 1.881 | 2.600 | 0.320 |
| 0.5 | 1.221 | 1.207 | 1.269 | 0.263 |
| 0.25 | 0.697 | 0.669 | 0.934 | 0.222 |
| 0.13 | 0.404 | 0.385 | 0.772 | 0.185 |
| 0.06 | 0.250 | 0.269 | 0.703 | 0.157 |
| 0.03 | 0.171 | 0.203 | 0.663 | 0.136 |
| 0.015 | 0.135 | 0.170 | 0.646 | 0.133 |
| 0.007 | 0.119 | 0.153 | 0.641 | 0.123 |
| 0.003 | 0.111 | 0.152 | 0.628 | 0.124 |
| Control | 0.087 | 0.145 | 0.635 | 0.126 |

EXAMPLE 3

Solution Assay for Glucose-6-Phosphate Dehydrogenase

This example demonstrates the determination of glucose-6-phosphate dehydrogenase with the present invention.

An aqueous reagent solution containing 0.005 molar ferrozine (LIG$_2$), 0.001 molar N-(3-hydroxy-2-pyridylmethyl)iminodiacetic acid (LIG$_1$), and 0.001 molar Fe(NO$_3$)$_3$.9H$_2$O was prepared. This solution was diluted 1:5 with an aqueous solution containing 7 millimolar MgCl$_2$, 2 millimolar glucose-6-phosphate, and 1 millimolar NAD and its pH was adjusted to 7.0.

A solution of glucose-6-phosphate dehydrogenase (842 I.U./l) was serially two-fold diluted to yield solutions containing enzyme activity ranging from 842 to 26 I.U./l. Fifty microliters of each enzyme solution and 50 µl of 0.2 millimolar phenazine methosulfate (ETA) were added to separate 900 µl aliquots of the above chelate solution. The change in absorbance at 560 nm was measured for each solution. A graph of enzyme activity plotted against enzyme rate as measured by absorbance change (A$_{560}$/min) is shown in FIG. 1. In the context of this disclosure, I.U. represents the International Unit for enzyme activity defined as one I.U. being the amount of enzyme activity required to catalyze the conversion of 1 micromole of substrate per minute under standard pH and temperature conditions for the given enzyme. Enzyme activity can be measured using conventional procedures.

The data presented in FIG. 1 clearly demonstrate the utility of the method of the present invention for enzyme analysis.

EXAMPLE 4

Dry Analytical Element for NADH Determination

A dry analytical element was prepared according to the present invention for determination of NADH. This element had the format and components as illustrated below.

|  |  | Range |
|---|---|---|
| Spreading Reagent Layer | Barium sulfate | 10–600 g/m² |
|  | Cellulose acetate | 8–50 g/m² |
|  | Estane TM | 0.1–10 g/m² |
|  | Triton TM X-100 surfactant | 0.1–20 g/m² |
|  | Phenazine methosulfate (ETA) | 0.001–0.3 g/m² |
| Subbing Layer | Poly(N—isopropylacrylamide) | 0.04–4 g/m² |
| Registration/ Reagent Layer | Gelatin (hardened) | 10–45 g/m² |
|  | Triton TM X-100 surfactant | 0.02–2 g/m² |
|  | Ferrozine (LIG$_2$) | 0.05–5 g/m² |
|  | N—(3-hydroxy-2-pyridyl-methyl)iminodiacetic acid (LIG$_1$) | 0.02–6 g/m² |
|  | Fe(NO$_3$)$_3$.9H$_2$O | 0.04–4 g/m² |
|  | KH$_2$PO$_4$ buffer (pH 6.5) | 0.1–10 g/m² |
|  | Poly(ethylene terephthalate) Support |  |

Figure 2:
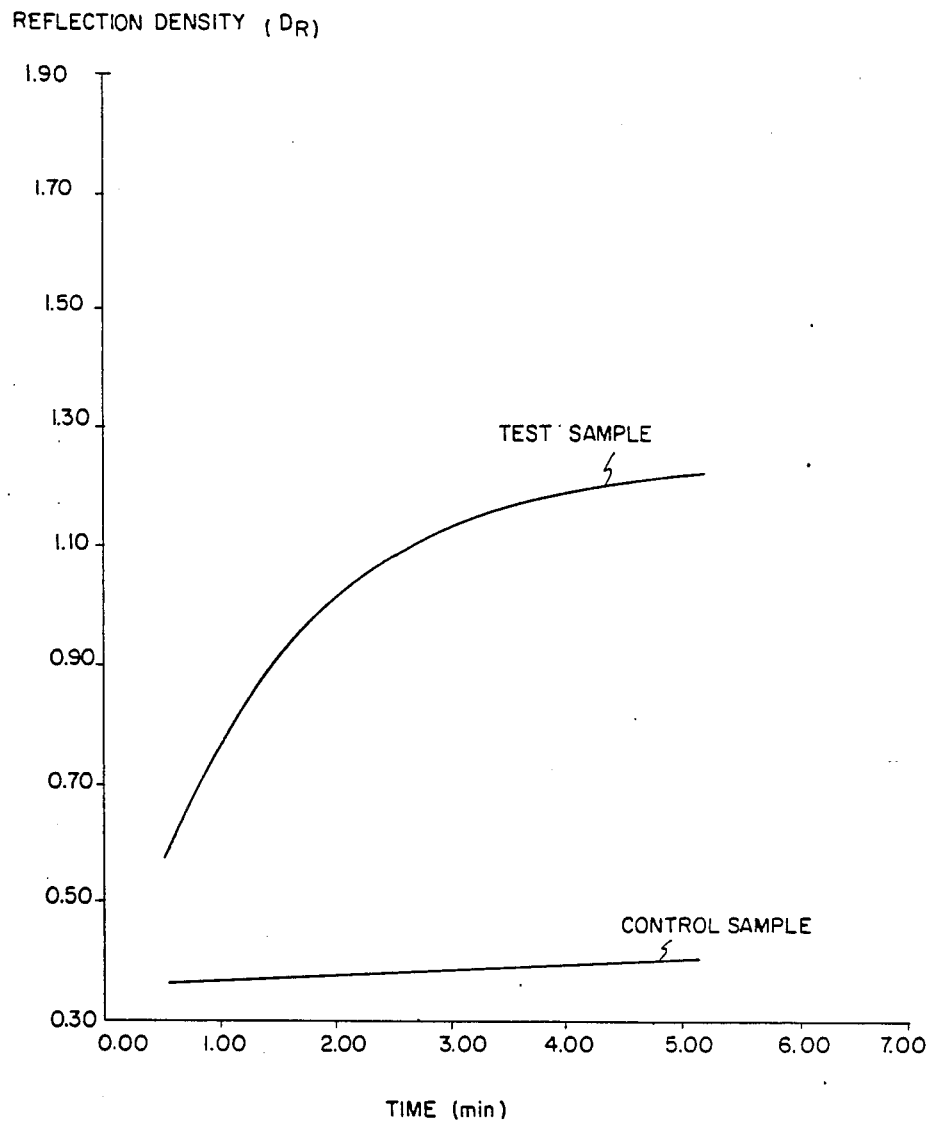
FIG. 2 is a graphical plot of reflection density ($D_R$) vs. time (min.) for a determination of NADH using a dry analytical element of this invention. This figure is discussed in Example 4 below.

Ten μl each of distilled water (Control sample) and of a 1 millimolar NADH solution (test sample) were spotted onto individual samples of this element, and the reflection density ($D_R$) was measured at 560 nm. Plots of $D_R$ vs. time (min.) for the Control and test samples are shown in FIG. 2. These results indicate that this element can be used to determine NADH.

EXAMPLE 5

Dry Analytical Element for Determination of Theophylline

A dry analytical element for the determination of theophylline was prepared having the format and components as illustrated below.

|  |  | Range |
|---|---|---|
| Spreading Layer | Barium sulfate | 10–600 g/m² |
|  | Cellulose acetate | 8–50 g/m² |
|  | Estane TM | 0.1–50 g/m² |
|  | Triton TM X-100 surfactant | 0.1–20 g/m² |
|  | Phenazine methosulfate (ETA) | 0.001–0.3 g/m² |
|  | KH$_2$PO$_4$ buffer (pH 6.5) | 0–20 g/m² |
|  | Theophylline antibodies containing 0.1% bovine serum albumin, diluted 1:20 | 0.001–0.2 L/m² |
|  | Glucose-6-phosphate | 0.05–5 g/m² |
| Subbing Layer | Poly(N—isopropylacrylamide) | 0.04–4 g/m² |
| Registration/ Reagent Layer | Hardened gelatin | 10–45 g/m² |
|  | Triton TM X-100 surfactant | 0.02–2 g/m² |
|  | Fe(NO$_3$)$_3$.9H$_2$O | 0.04–4 g/m² |
|  | Ferrozine (LIG$_2$) | 0.05–5 g/m² |
|  | N—(3-hydroxy-2-pyridyl-methyl)iminodiacetic acid (LIG$_1$) | 0.02–2 g/m² |
|  | KH$_2$PO$_4$ buffer (pH 6.5) | 0.1–10 g/m² |
|  | Poly(ethylene terephthalate) Support |  |

Ten μl each of the following fluids were spotted onto samples of this element:

Test Solution A: prepared from 60 μl of Syva EMIT TM Enzyme Reagent B for theophylline, available from Syva Co. (Palo Alto, Calif.), 10 μl Syva theophylline calibrator fluid, and 130 μl 2 millimolar NAD in distilled water;

Test Solution B: 1 millimolar NADH in distilled water; and

Control: Distilled water.

Figure 3:
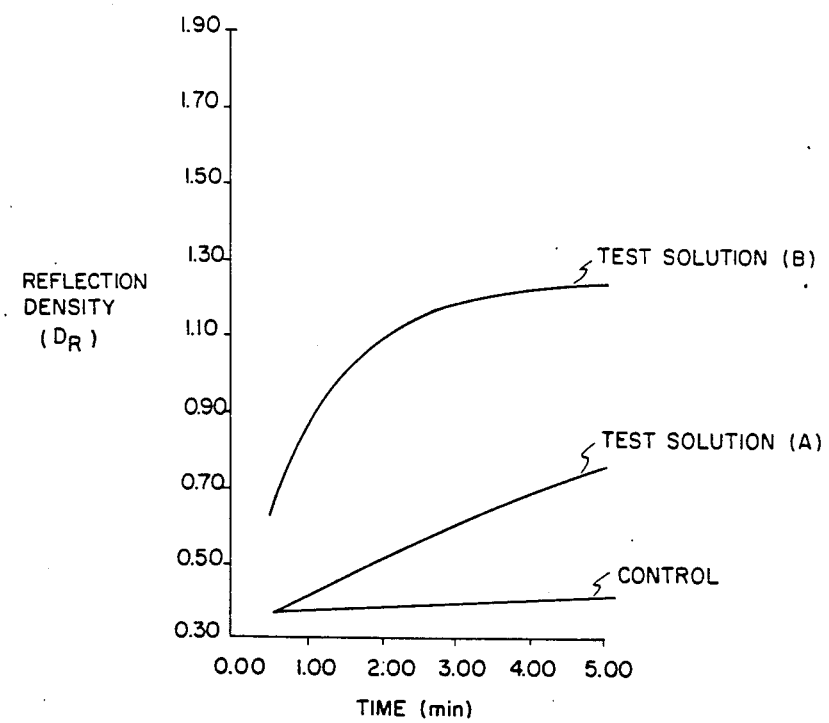
FIG. 3 is a graphical plot of reflection density ($D_R$) vs. time (min.) for the determination of theophylline using a dry analytical element. This figure is discussed in Example 5 below.

The reflection density ($D_R$) was then measured at 560 nm with a conventional spectrophotometer. The results are illustrated in FIG. 3 which is a plot of $D_R$ vs. time. This plot indicates the usefulness of the present invention for determining theophylline in a dry analytical element.

The invention has been described in detail with particular reference to preferred embodiments thereof, but it will be understood that variations and modifications can be effected within the spirit and scope of the invention.

We claim:

1. A dry analytical element for the determination of a reductant in a liquid, said element comprising: a support having thereon one or more coated layers, any of said layers containing any or all of
   (a) a chelate of ferric ions and a ferric coordinating ligand (LIG$_1$) which produces ferrous ions when reduced,
   (b) a ferrous ion coordinating ligand (LIG$_2$) which preferentially coordinates ferrous ions to form a colored complex,
   (c) an electron transfer agent, and
   (d) a buffer to maintain the assay pH at 6.5 or above, and wherein all of the components (a), (b), (c), and (d) are contained in said element.

2. A method for the determination of a reductant in a liquid, said method comprising the steps of:
   A. physically contacting a sample of said liquid with the element of claim 1 at or above a pH of 6.5 to form a colored complex in said element, and
   B. detecting said colored complex.

3. The method of claim 2 wherein said element contains an iminodiacetic acid derivative as a ferric ion coordinating ligand LIG$_1$.

4. The method of claim 2 wherein said element contains a ferrous ion coordinating ligand (LIG$_2$) which has a coordinating moiety represented by the structure:

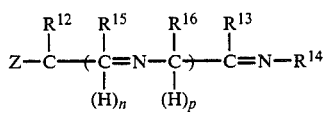

wherein m is 0 or a positive integer of 1 to 3, n and p are independently 0 or 1, == represents a single or double bond, Z is monovalent or divalent and is R''—N=, O=, S=, R''—P=, (R'')$_2$P— or (R'')$_3$P=, and when Z is (R'')$_2$P—, n is 1, otherwise n is 0, R'', R$^{12}$, R$^{13}$, R$^{14}$, R$^{15}$ and R$^{16}$ are independently hydrogen, amino, hydroxy, mercapto, alkoxy, alkyl, aryl or a heterocyclic moiety, and when R$^{16}$ is so defined, p is 1 and == is a single bond, if m is 0, R'' and R$^{12}$, R$^{12}$ and R$^{13}$, and R$^{13}$ and R$^{14}$, taken together, can independently represent the carbon atoms and heteroatoms necessary to complete a substituted or unsubstituted heterocyclic nucleus, or R$^{12}$ and R$^{13}$, taken together can represent the carbon atoms or heteroatoms necessary to complete a substituted or unsubstituted carbocyclic or heterocyclic nucleus, or if m is 1 to 3, R'' and R$^{12}$, R$^{15}$ and R$^{16}$ and R$^{13}$ and R$^{14}$, taken together, can independently represent the carbon and heteroatoms necessary to complete a substituted or unsubstituted heterocyclic nucleus.

5. The method of claim 2 wherein said element contains an interactive composition which reacts with an analyte in said sample to produce either NADH or NADPH.

6. A dry analytical element for the determination of nicotinamide adenine dinucleotide, reduced form (NADH) or nicotinamide adenine dinucleotide phosphate, reduced form (NADPH), or of an analyte which can react to produce either NADH or NADPH in the presence of NAD+ or NADP+, respectively, in a liquid, said element comprising:

a support having thereon a coated porous spreading layer, and one or more additional coated layers, and in any of said coated layers, any or all of:

(a) a chelate of ferric ions and a ferric coordinating ligand (LIG$_1$) which produces ferrous ions when reduced, (b) a buffer to maintain the assay pH at 6.5 or above, (c) an electron transfer agent, and (d) a ferrous ion coordinating ligand (LIG$_2$) which coordinates ferrous ions to form a colored complex, said ligand (LIG$_2$) having a coordinating moiety represented by the structure:

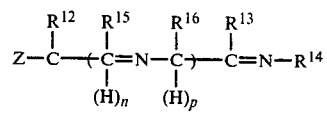

wherein m is 0 or a positive integer of 1 to 3, n and p are independently 0 or 1, == represents a single or double bond, Z is monovalent or divalent and is R''—N=, O=, S=, R''—P=, (R'')$_2$P— or (R'')$_3$P=, and when Z is (R'')$_2$P—, n is 1, otherwise n is 0, R'', R$^{12}$, R$^{13}$, R$^{14}$, R$^{15}$ and R$^{16}$ are independently hydrogen, amino, hydroxy, mercapto, alkoxy, alkyl, aryl or a heterocyclic moiety, and when R$^{16}$ is so defined, p is 1 and == is a single bond, if m is 0, R'' and R$^{12}$, R$^{12}$ and R$^{13}$, and R$^{13}$ and R$^{14}$, taken together, can independently represent the carbon atoms and heteroatoms necessary to complete a substituted or unsubstituted heterocyclic nucleus, or R$^{12}$ and R$^{13}$, taken together can represent the carbon atoms or heteroatoms necessary to complete a substituted or unsubstituted carbocyclic or heterocyclic nucleus, or if m is 1 to 3, R'' and R$^{12}$, R$^{15}$ and R$^{16}$ and R$^{13}$ and R$^{14}$, taken together, can independently represent the carbon and heteroatoms necessary to complete a substituted or unsubstituted heterocyclic nucleus, and wherein all of the components (a), (b), (c), and (d) are contained in said element.

7. The element of claim 6 wherein m is 0 or 1 and Z is R''—N=.

8. The element of claim 6 wherein LIG$_1$ is an iminodiacetic acid derivative.

9. The element of claim 6 comprising an interactive composition for said analyte.

* * * * *